United States Patent
Baek et al.

(10) Patent No.: US 11,382,887 B2
(45) Date of Patent: Jul. 12, 2022

(54) OPHTHALMIC COMPOSITION FOR GLAUCOMA TREATMENT

(71) Applicant: YS LIFE SCIENCE CO., LTD., Seoul (KR)

(72) Inventors: Areum Baek, Suwon-si (KR); Youngsik Chung, Yongin-si (KR); Hyun Ik Shin, Suwon-si (KR); Chang Young Oh, Seongnam-si (KR); Kee Young Lee, Seoul (KR)

(73) Assignee: YS LIFE SCIENCE CO. LTD., Seoul (KR)

( * ) Notice: Subject to any disclaimer, the term of this patent is extended or adjusted under 35 U.S.C. 154(b) by 201 days.

(21) Appl. No.: 16/624,560

(22) PCT Filed: Jun. 21, 2018

(86) PCT No.: PCT/KR2018/007000
§ 371 (c)(1),
(2) Date: Dec. 19, 2019

(87) PCT Pub. No.: WO2018/236158
PCT Pub. Date: Dec. 27, 2018

(65) Prior Publication Data
US 2020/0129468 A1    Apr. 30, 2020

(30) Foreign Application Priority Data

Jun. 22, 2017 (KR) .................. 10-2017-0079292

(51) Int. Cl.
| *A61K 31/216* | (2006.01) |
| *A61K 47/38* | (2006.01) |
| *A61K 47/32* | (2006.01) |
| *A61K 31/165* | (2006.01) |
| *A61P 27/06* | (2006.01) |

(52) U.S. Cl.
CPC .......... *A61K 31/216* (2013.01); *A61K 31/165* (2013.01); *A61K 47/32* (2013.01); *A61K 47/38* (2013.01); *A61P 27/06* (2018.01)

(58) Field of Classification Search
CPC .... A61K 31/216; A61K 31/165; A61K 47/32; A61K 47/38; A61P 27/06
USPC .......................................................... 514/530
See application file for complete search history.

(56) References Cited

U.S. PATENT DOCUMENTS

| 6,531,614 B2 | 3/2003 | Conrow |
| 2009/0170944 A1 | 7/2009 | Lambert et al. |
| 2012/0184552 A1 | 7/2012 | Nakajima et al. |
| 2017/0049697 A1* | 2/2017 | Barman ................. A61P 27/02 |

FOREIGN PATENT DOCUMENTS

| JP | 2008-528490 | 7/2008 |
| JP | 2013-511494 | 4/2013 |
| JP | 2014-520895 | 8/2014 |
| KR | 10-2008-0005825 A | 1/2008 |
| KR | 10-2010-0134682 A | 12/2010 |
| KR | 10-2013-0112728 A | 10/2013 |
| KR | 10-2016-0102319 A | 8/2016 |
| WO | 2016/063184 | 4/2016 |

OTHER PUBLICATIONS

International Search Report for PCT/KR2018/007000 dated Nov. 13, 2018 [PCT/ISA/210].

* cited by examiner

*Primary Examiner* — Kristin A Vajda
(74) *Attorney, Agent, or Firm* — Sughrue Mion, PLLC

(57) ABSTRACT

An eye drop composition for treating glaucoma is disclosed. The eye drop composition includes a prostaglandin analogue, a thickening agent, and a solubilizing agent, wherein the thickening agent is carboxymethylcellulose or a salt thereof, and the solubilizing agent is tyloxapol.

6 Claims, No Drawings

OPHTHALMIC COMPOSITION FOR GLAUCOMA TREATMENT

CROSS REFERENCE TO RELATED APPLICATIONS

This application is a National Stage of International Application No. PCT/KR2018/007000 filed Jun. 21, 2018, claiming priority based on Korean Patent Application No. 10-2017-0079292 filed Jun. 22, 2017.

TECHNICAL FIELD

The present invention relates to an eye drop composition for treating glaucoma, and more particularly an eye drop composition for treating glaucoma which has little dry eye side effects and is stable at room temperature.

BACKGROUND ART

Glaucoma is a disease which causes abnormalities of optic nerve function such as optic nerve atrophy, visual field defects, and loss of visual acuity due to an increase in intraocular pressure, and it occurs when there is an abnormality in the generation and discharge of aqueous humor. Usually, when there is an abnormality in the pathway of discharge, the disease occurs.

The therapeutic agent for glaucoma includes prostaglandin analogues, beta blockers, carbonic anhydrase inhibitors, sympathomimetic agents, parasympathetic agonists, and the like. In particular, latanoprost is a prostaglandin analogue (PGA) and is used as a first-line therapeutic agent for glaucoma, and this is known for having the great effect of intraocular pressure reduction and the high medication compliance. In addition, tafluprost is a recently developed drug and is known as a drug which has a similar intraocular pressure reduction effect to that of the conventional latanoprost.

However, although glaucoma is a disease in which continuous drug treatment is important, the glaucoma treatment causes adverse effects such as induction of ocular inflammation and induction of ocular dryness due to a preservative such as benzalkonium chloride contained in an eye drop composition, which hinders the long-term treatment of patients. The benzalkonium chloride is nitrogen cationic surfactant belonging to a quaternary ammonium salt and serves not only as a preservative but also as a surfactant to prevent a prostaglandin analogue from being adsorbed on the resin of a container. Further, it has the effect of increasing the absorption rate of the drug, but it also has toxic effects such as irritation, induction of inflammation, and induction of dry eye. Thus, recently, development of an eye drop composition for treating glaucoma which does not contain a preservative has been advanced [see Korean Patent Laid-open Publication No. 10-2016-0102319].

However, when an eye drop composition without preservatives such as benzalkonium chloride is stored at room temperature, the stability is not ensured and thus both Xalatan® and Taflotan®-S which are preservative-free single dose eye drop compositions have been sold in refrigerated storage.

DISCLOSURE

Technical Problem

It is an object of the present invention to provide an eye drop composition for treating glaucoma which has little dry eye side effects and is stable at room temperature.

Technical Solution

In one aspect, the present invention provides an eye drop composition for treating glaucoma, comprising a prostaglandin analogue, a thickening agent and a solubilizing agent, wherein the thickening agent is carboxymethylcellulose or a salt thereof, and the solubilizing agent is tyloxapol.

In one embodiment of the present invention, the prostaglandin analogue may be at least one selected from the group consisting of latanoprost, tafluprost, unoprostone, travoprost, and bimatoprost.

In another embodiment of the present invention, the carboxymethylcellulose or a salt thereof may have a viscosity of a 2% aqueous solution at 20° C. of 25 to 800 cPs.

In still another embodiment of the present invention, the tyloxapol may be contained in an amount of 0.01 to 1% (w/v) based on the entire eye drop composition for treating glaucoma.

In other embodiment of the present invention, the eye drop composition for treating glaucoma may comprise no preservative.

Advantageous Effects

The eye drop composition for treating glaucoma according to the present invention contains carboxymethylcellulose or a salt thereof as a thickening agent and tyloxapol as a solubilizing agent, and thus it is stable at room temperature with little dry eye side effect. In particular, the eye drop composition for treating glaucoma according to the present invention is stable at room temperature even without substantially containing a preservative, and thus it can be commercialized in a form which can be stored at room temperature.

BEST MODE

Hereinafter, the present invention will be described in more detail.

One embodiment of the present invention relates to an eye drop composition for treating glaucoma, comprising a prostaglandin analogue, a thickening agent and a solubilizing agent, wherein the thickening agent is carboxymethylcellulose or a salt thereof, and the solubilizing agent is tyloxapol.

In one embodiment of the present invention, the prostaglandin analogue can be used without limitation as long as it can be used for the treatment of glaucoma showing the effect of intraocular pressure reduction. Specifically, as the prostaglandin analogue, latanoprost, tafluprost, unoprostone, travoprost, bimatoprost and the like may be used alone or in combination of two or more. In terms of stability and efficacy, the prostaglandin analogue may be at least one of latanoprost, tafluprost, and bimatoprost.

The content of the prostaglandin analogue may be selected depending on the kind of the prostaglandin analogue, the degree of the symptom, and the like, and specifically, it may be 0.0001 to 0.2% (w/v) based on the entire eye drop composition for treating glaucoma.

In one embodiment of the present invention, the thickening agent is carboxymethylcellulose or a salt thereof. The carboxymethylcellulose or a salt thereof performs the role of increasing the viscosity of the eye drop composition to delay the discharge of the main component from the eye, to increase the retention time of the main component, and to increase bioavailability in the external eye tissues. In addition, the carboxymethylcellulose or a salt thereof exhibits therapeutic activity for dry eye syndrome, and it can reduce the side effects of dry eye syndrome which may occur during long-term administration.

In particular, the carboxymethylcellulose or a salt thereof is used in combination with tyloxapol as a solubilizing agent described later, and thereby, it is possible to prevent the prostaglandin analogue from being adsorbed on the resin of the container and to effectively suppress the generation of the related substance, even without a separate preservative such as benzalkonium chloride. Accordingly, the eye drop composition for treating glaucoma according to one embodiment of the present invention has little dry eye side effect caused by a preservative and is stable at room temperature, and thus it can be commercialized in a form which can be stored at room temperature.

In one embodiment of the present invention, the salt of carboxymethylcellulose may be pharmaceutically acceptable alkali metal salts, alkali earth metal salts, and the like, but is not limited thereto. For example, a sodium salt, a calcium salt, and the like can be used.

The carboxymethylcellulose or a salt thereof may have a viscosity of a 2% aqueous solution at 20° C. of 25 to 800 cPs, preferably 25 to 200 cPs. When the viscosity of a 2% aqueous solution at 20° C. of the carboxymethylcellulose or a salt thereof is less than 25 cPs, the effect of the thickening agent may be insufficient due to the low viscosity. When the viscosity exceeds 800 cPs, sterile filtration may be difficult due to the high viscosity.

The viscosity of the eye drop composition for treating glaucoma may be controlled depending on the viscosity of the carboxymethylcellulose or a salt thereof.

In one embodiment of the present invention, the eye drop composition for treating glaucoma may have a viscosity at 20° C. of 3 to 15 cPs, preferably 8 to 12 cPs. When the viscosity at 20° C. of the eye drop composition for treating glaucoma is less than 3 cPs, the stability of the drug may be lowered or the muco-adhesiveness of the drug may be decreased. When the viscosity exceeds 15 cPs, delayed drug release and visual blurring may occur due to high viscosity.

The viscosity can be obtained from Brookfield rotational viscometer measurement.

In one embodiment of the present invention, the content of carboxymethylcellulose or a salt thereof may be 0.1 to 1% (w/v), preferably 0.1 to 0.5% (w/v) based on the entire eye drop composition for treating glaucoma. When the content of carboxymethylcellulose or a salt thereof is less than 0.1% (w/v), the effect of the thickening agent may be insufficient due to the low viscosity, and when it exceeds 1% (w/v), sterile filtration may be difficult due to the high viscosity.

In one embodiment of the present invention, the solubilizing agent is tyloxapol. The tyloxapol plays a role in increasing a water solubility of the prostaglandin analogue. Tyloxapol possesses a polar group in a molecule although the hydrophilic group is not charged, and thus it has good affinity with water, and little irritation to the eye, so that it can be advantageously used for long-term treatment.

In particular, when the tyloxapol is used in combination with carboxymethylcellulose or a salt thereof as described above, the solubilizing effect can be enhanced to stabilize the eye drop composition for treating glaucoma at room temperature even without a separate preservative such as benzalkonium chloride.

The content of tyloxapol may vary depending on the kind of prostaglandin analogues, and may be 0.01 to 1% (w/v), preferably 0.05 to 0.5% (w/v) based on the entire eye drop composition for treating glaucoma. When the content of tyloxapol is less than 0.01% (w/v), the container adsorption of the drug may increase or the stability of the drug may decrease. When the content of tyloxapol is more than 1% (w/v), a decrease in drug absorption or a corneal damage can occur.

The eye drop composition for treating glaucoma according to an embodiment of the present invention may further include an isotonic agent, a buffer, a pH adjusting agent and/or an antioxidant, etc.

The isotonic agent acts to make the osmotic pressure of the eye drop composition similar to the osmotic pressure in the body so that the eye drop composition is sufficiently absorbed into the eye.

Examples of the isotonic agent include mannitol, sodium chloride, potassium chloride, calcium chloride, glycerin, propylene glycol, sorbitol, glucose, etc. They may be used alone or in combination of two or more. In view of improvement of the absorption rate, mannitol, sodium chloride and/or glycerin are particularly preferred.

The content of the isotonic agent may be 0.3 to 3% (w/v) based on the entire eye drop composition for treating glaucoma. When the content of the isotonic agent is less than 0.3% (w/v), a decrease in drug absorption may occur due to hypotonicity, and when the content of the isotonic agent is greater than 3% (w/v), side effects such as dehydration of the eye may occur due to hypertonicity.

The buffer and the pH adjusting agent perform the role of further improving the stability of the prostaglandin analogue at room temperature and reducing the occurrence of latanoprost acid, tafluprost acid, bimatoprost acid, etc, which are related substances.

The buffer may be sodium dihydrogen phosphate, sodium monohydrogen phosphate, boric acid, citric acid, ε-aminocaproic acid, sodium hydrogen phosphate heptahydrate, sodium citrate and the like. They can be used alone or in combination of two or more.

As the pH adjusting agent, acids such as hydrochloric acid, lactic acid, citric acid, phosphoric acid and acetic acid; or alkalis such as sodium hydroxide, potassium hydroxide, sodium carbonate and sodium hydrogen carbonate may be used.

The pH of the eye drop composition for treating glaucoma according to an embodiment of the present invention is preferably adjusted to 5.5 to 7.5 in terms of the stability at room temperature.

As the antioxidant, edetic acid and the like may be used, and the content thereof may be 0.01 to 0.1% (w/v).

In one embodiment of the present invention, the eye drop composition for treating glaucoma may not contain a preservative. At this time, the eye drop composition for treating glaucoma can be formulated into a single dose form which can be stored at room temperature.

In another embodiment of the present invention, the eye drop composition for treating glaucoma may contain a preservative. At this time, the eye drop composition for treating glaucoma can be formulated into a multidose form which can be stored at room temperature. In this case, as the preservative, benzalkonium chloride, sorbic acid, potassium sorbate, methyl parahydroxybenzoate, ethyl parahydroxybenzoate, butyl parahydroxybenzoate, and the like may be used alone or in a combination of two or more.

The eye drop composition for treating glaucoma according to an embodiment of the present invention may be prepared through the following steps:

a first step of dissolving a buffer in sterile purified water;

a second step of sequentially dissolving an isotonic agent, tyloxapol, carboxymethylcellulose or a salt thereof in the solution; and a third step of dissolving a prostaglandin analogue in the solution.

After the third step, a fourth step of adjusting the pH of the solution and filtering the solution may be further performed.

It is preferable that the first to fourth steps are sequentially performed in order to prevent the occurrence of precipitation of carboxymethylcellulose or a salt thereof.

In the third step, the prostaglandin analogue-containing solution may be heated to 50 to 70° C. to completely dissolve the prostaglandin analogue.

Hereinafter, the present invention will be described in more detail with reference to examples, comparative examples and experimental examples. It should be apparent to those skilled in the art that these examples, comparative examples and experimental examples are given for illustrative purposes only and are not intended to limit the scope of the present invention.

Examples 1 to 3 and Comparative Examples 1 to 5: Preparation of Latanoprost Eye Drop Composition Latanoprost eye drop compositions were prepared in accordance with the following method using the composition shown in Table 1 below (unit: %, w/v).

Sodium dihydrogen phosphate and sodium monohydrogen phosphate were added and dissolved in sterile purified water (900 mL). Then, mannitol, tyloxapol and sodium carboxymethylcellulose were dissolved in order and latanoprost was added thereto. Then, the temperature was raised to 60° C. to completely dissolve latanoprost, and the eye drop composition was cooled to room temperature, confirming that latanoprost was completely dissolved. The pH was adjusted to pH 6.0 by adding a suitable quantity of 1N hydrochloric acid, and the total amount of the composition was adjusted to 1000 mL with sterile purified water. Subsequently, the composition was sterile-filtered (PES membrane filter, 0.2 μm).

TABLE 1

| Category | Component | Ex. 1 | Ex. 2 | Ex. 3 | Comp. Ex. 1 | Comp. Ex. 2 | Comp. Ex. 3 | Comp. Ex. 4 | Comp. Ex. 5 |
|---|---|---|---|---|---|---|---|---|---|
| Main component | Latanoprost | 0.005 | 0.005 | 0.005 | 0.005 | 0.005 | 0.005 | 0.005 | 0.005 |
| Thickening agent | Sodium carboxymethyl cellulose | 0.5 | 0.5 | 0.5 | — | — | — | 0.5 | — |
| | Hydroxypropyl methyl cellulose | — | — | — | 0.3 | — | — | — | — |
| | Poloxamer 188 | — | — | — | — | 0.1 | — | — | — |
| | Poloxamer 407 | — | — | — | — | — | 0.1 | — | — |
| Isotonic agent | Mannitol | 2.9 | 2.9 | 2.9 | 2.9 | 2.9 | 2.9 | 2.9 | 2.9 |
| Solubilizing agent | tyloxapol | 0.3 | 0.05 | 0.1 | 0.05 | 0.05 | 0.05 | — | 0.3 |
| Buffer | sodium dihydrogen phosphate | 0.64 | 0.64 | 0.64 | 0.64 | 0.64 | 0.64 | 0.64 | 0.64 |
| | sodium monohydrogen phosphate | 0.19 | 0.19 | 0.19 | 0.19 | 0.19 | 0.19 | 0.19 | 0.19 |
| pH adjusting agent | 1N hydrochloric acid | q.s. | q.s. | q.s. | q.s. | q.s. | q.s. | q.s. | q.s. |
| | Sterile purified water | Balance | Balance | Balance | Balance | Balance | Balance | Balance | Balance |

Examples 4 to 9: Preparation of Latanoprost Eye Drop Composition

Latanoprost eye drop compositions were prepared in accordance with the following method using the composition shown in Table 2 below while varying the viscosity of the eye drop composition and the content of the solubilizing agent (unit: %, w/v).

Sodium dihydrogen phosphate and sodium monohydrogen phosphate were added and dissolved in sterile purified water (900 mL). Then, sodium chloride, tyloxapol and sodium carboxymethylcellulose were dissolved in order and latanoprost was added thereto. Then, the temperature was raised to 60° C. to completely dissolve latanoprost, and the eye drop composition was cooled to room temperature, confirming that latanoprost was completely dissolved. The pH was adjusted to pH 6.0 by adding a suitable quantity of 1N hydrochloric acid, and the total amount of the composition was adjusted to 1000 mL with sterile purified water. Subsequently, the composition was sterile-filtered (PES membrane filter, 0.2 μm).

TABLE 2

| Category | Component | Ex. 4 | Ex. 5 | Ex. 6 | Ex. 7 | Ex. 8 | Ex. 9 |
|---|---|---|---|---|---|---|---|
| Main component | Latanoprost | 0.005 | 0.005 | 0.005 | 0.005 | 0.005 | 0.005 |
| Thickening agent | Sodium carboxymethyl cellulose | 0.5 | 0.5 | 0.5 | 0.5 | 0.5 | 0.5 |
| Isotonic agent | Sodium chloride | 0.45 | 0.45 | 0.45 | 0.45 | 0.45 | 0.45 |
| Solubilizing agent | Tyloxapol | 0.05 | 0.1 | 0.05 | 0.1 | 0.05 | 0.1 |
| Buffer | Sodium dihydrogen phosphate | 0.64 | 0.64 | 0.64 | 0.64 | 0.64 | 0.64 |
|  | Sodium monohydrogen phosphate | 0.19 | 0.19 | 0.19 | 0.19 | 0.19 | 0.19 |
| PH adjusting agent | 1N hydrochloric acid | q.s. | q.s. | q.s. | q.s. | q.s. | q.s. |
|  | Sterile purified water | Balance | Balance | Balance | Balance | Balance | Balance |
|  | Viscosity of eye drop composition (20° C., unit: cPs) | 3 | 3 | 5 | 5 | 10 | 10 |
|  | Viscosity of sodium carboxy methyl cellulose (20° C., 2%, unit: cPs) | 25-50 | 25-50 | 50-100 | 50-100 | 50-100 | 50-100 |

Examples 10 to 12 and Comparative Examples 6 to 7: Preparation of Tafluprost Eye Drop Composition Tafluprost eye drop compositions were prepared in accordance with the following method using the composition shown in Table 3 below (unit: %, w/v).

Sodium dihydrogen phosphate was added and dissolved in sterile purified water (900 mL). Then, glycerin, tyloxapol, edetic acid and sodium carboxymethylcellulose were dissolved in order and tafluprost was added thereto. Then, the temperature was raised to 60° C. to completely dissolve tafluprost, and the eye drop composition was cooled to room temperature, confirming that tafluprost was completely dissolved. The pH was adjusted to pH 6.0 by adding a suitable quantity of 1N sodium hydroxide, and the total amount of the composition was adjusted to 1000 mL with sterile purified water. Subsequently, the composition was sterile-filtered (PES membrane filter, 0.2 μm).

TABLE 3

| Category | Component | Ex. 10 | Ex. 11 | Ex. 12 | Comp. Ex. 6 | Comp. Ex. 7 |
|---|---|---|---|---|---|---|
| Main component | Tafluprost | 0.0015 | 0.0015 | 0.0015 | 0.0015 | 0.0015 |
| Thickening agent | Sodium carboxymethylcellulose | 0.5 | 0.5 | 0.5 | 0.5 | — |
| Isotonic agent | Glycerin | 2.25 | 2.25 | 2.25 | 2.25 | 2.25 |
| Solubilizing agent | Tyloxapol | 0.3 | 0.1 | 0.2 | — | 0.3 |

TABLE 3-continued

| Category | Component | Ex. 10 | Ex. 11 | Ex. 12 | Comp. Ex. 6 | Comp. Ex. 7 |
|---|---|---|---|---|---|---|
| Antioxidant | Edetic acid | 0.05 | 0.05 | 0.05 | 0.05 | 0.05 |
| Buffer | sodium dihydrogon phosphate | 0.2 | 0.2 | 0.2 | 0.2 | 0.2 |
| pH adjusting agent | 1N NaOH | q.s. | q.s. | q.s. | q.s. | q.s. |
| | Sterile purified water | Balance | Balance | Balance | Balance | Balance |

Example 13: Preparation of Bimatoprost Eye Drop Composition

Bimatoprost eye drop composition was prepared in accordance with the following method using the composition shown in Table 4 below (unit: %, w/v).

Sodium chloride, tyloxapol, sodium citrate, sodium hydrogen phosphate heptahydrate and sodium carboxymethylcellulose were sequentially dissolved in sterile purified water (900 mL), and bimatoprost was added thereto. Then, the temperature was raised to 60° C. to completely dissolve bimatoprost, and the eye drop composition was cooled to room temperature, confirming that bimatoprost was completely dissolved. The pH was adjusted to pH 7.0-7.2 by adding a suitable quantity of 1N hydrochloric acid, and the total amount of the composition was adjusted to 1000 mL with sterile purified water. Subsequently, the composition was sterile-filtered (PES membrane filter, 0.2 μm).

TABLE 4

| Category | Component | Ex. 13 |
|---|---|---|
| Main component | Bimatoprost | 0.01 |
| Thickening agent | Sodium carboxymethylcellulose | 0.5 |
| Isotonic agent | Sodium chloride | 0.81 |
| Solubilizing agent | Tyloxapol | 0.3 |
| Buffer | Sodium hydrogen phosphate heptahydrate | 2.68 |
| Buffer | Sodium citrate | 0.14 |
| pH adjusting agent | 1N HCl | q.s. |
| | Sterile purified water | Balance |

Experimental Example 1: Stability of Latanoprost Eye Drop Composition According to the Type of Thickening Agent The eye drop compositions of Example 2 and Comparative Examples 1 to 3 stored in an LDPE container were stored for 2 months under semi-permeable container accelerated storage conditions (40° C., relative humidity 25%), and changes in the contents of latanoprost were confirmed. The content of latanoprost was analyzed using high performance liquid chromatography (HPLC). The results are shown in Table 5 below.

TABLE 5

| | Ex. 2 | Comp. Ex. 1 | Comp. Ex. 2 | Comp. Ex. 3 |
|---|---|---|---|---|
| Loss of latanoprost content due to container adsorption (wt %) | 5 | 15 | 17 | 13 |

From the results of Table 5 above, it can be seen that a rapid decrease in the content of latanoprost occurs except for Example 2 containing sodium carboxymethylcellulose.

Experimental Example 2: Stability of Latanoprost Eye Drop Composition According to the Content of Solubilizing Agent The eye drop compositions of Examples 1 to 3 stored in an LDPE container were stored for 2 months under semi-permeable container accelerated storage conditions (40° C., relative humidity 25%), and changes in the contents of latanoprost were confirmed. The content of latanoprost was analyzed using high performance liquid chromatography (HPLC). The results are shown in Table 6 below.

TABLE 6

| | Ex. 1 | Ex. 2 | Ex. 3 |
|---|---|---|---|
| Loss of latanoprost content due to container adsorption (wt %) | ≤1 | 5 | 2 |

From the results of Table 6 above, it can be seen that loss of the latanoprost content was small when tyloxapol was used at 0.1% or more.

Experimental Example 3: Stability of Latanoprost Eye Drop Composition According to the Presence or Absence of Thickening Agent and Solubilizing Agent The eye drop compositions of Example 1 and Comparative Examples 4 to 5 stored in an LDPE container were stored for 2 months under semi-permeable container accelerated storage conditions (40° C., relative humidity 25%), and changes in the contents of latanoprost and the generation of a related substance were confirmed. The content of latanoprost was analyzed using high performance liquid chromatography (HPLC). The results are shown in Table 7 below.

TABLE 7

| Component | Ex. 1 | Comp. Ex. 4 | Comp. Ex. 5 |
|---|---|---|---|
| Loss of latanoprost content due to container adsorption (wt %) | ≤1 | 24 | ≤1 |
| Generation amount of related substance (latanoprost acid) (wt %) | 0.5 | 1.5 | 1 |

From the results of Table 7 above, it can be seen that in the case of containing sodium carboxymethylcellulose but not containing tyloxapol (Comparative Example 4), a loss of the latanoprost content of 20% or more occurs, and in the case of containing tyloxapol but not containing sodium carboxymethylcellulose (Comparative Example 5), as compared with Example 1, a loss of the latanoprost content occurs similarly, but the generation of the related substance is equivalent to or larger than two times. Therefore, it can be seen that the loss of the latanoprost content and the generation amount of the related substance are minimum, when sodium carboxymethylcellulose and tyloxapol are contained together.

Experimental Example 4: Comparison of the Stability of the Latanoprost Eye Drop Composition of the Present Invention with Commercial Product The eye drop composition of Example 1, and commercially available products, a preservative (0.02%)-containing Xalatan® (Pfizer, stored at room temperature) and a preservative-free Xalatan® (Pfizer, stored under cold condition) stored in an LDPE container were stored for 2 months under semi-permeable container accelerated storage conditions (40° C., relative humidity 25%), and changes in the contents of latanoprost and the generation of a related substance were confirmed. The content of latanoprost was analyzed using high performance liquid chromatography (HPLC). The results are shown in Table 8 below.

TABLE 8

| | Ex. 1 | Preservative (0.02%)-containing Xalatan ® | Preservative-free Xalatan ® |
|---|---|---|---|
| Loss of latanoprost content due to container adsorption (wt %) | ≤1 | 13 | 18 |
| Generation amount of related substance (latanoprost acid) (wt %) | 0.5 | 1.7 | 3 |

From the results of Table 8 above, it can be seen that in the case of commercially available products, a preservative (0.02%)-containing Xalatan® and a preservative-free Xalatan®, latanoprost was adsorbed on the container resin, and thus, the content of latanoprost in the eye drop composition was greatly reduced. In particular, it can be seen that the preservative-free Xalatan® did not contain a preservative, and thus, the loss of the latanoprost content occurred significantly and also the generation amount of the related substance was equivalent to or larger than 1.5 times, as compared with the preservative (0.02%)-containing Xalatan®. In contrast, it can be seen that in the case of Example 1, the loss of the latanoprost content occurred within 1% and the related substance was generated less than the commercial products, and thus Example 1 was relatively stable under accelerated storage conditions.

Experimental Example 5: Stability of Latanoprost Eye Drop Composition According to the Viscosity of Thickening Agent and the Content of Solubilizing Agent The eye drop compositions of Examples 4 to 9 stored in an LDPE container were stored for 2 months under semi-permeable container accelerated storage conditions (40° C., relative humidity 25%), and the contents of latanoprost were confirmed. The latanoprost content was analyzed using high performance liquid chromatography (HPLC). The results are shown in Table 9 below.

TABLE 9

| | Ex. 4 | Ex. 5 | Ex. 6 | Ex. 7 | Ex. 8 | Ex. 9 |
|---|---|---|---|---|---|---|
| Loss of latanoprost content due to container adsorption (wt %) | 5.6 | 1.0 | 3.4 | 1.1 | 1.5 | ≤1 |

From the results of Table 9 above, it can be seen that the degree to which latanoprost was adsorbed and lost on the container resin was different depending on the viscosity of the thickening agent and the content of the solubilizing agent, and Example 9 showed the lowest decrease in the content of latanoprost.

Experimental Example 6: Effect of the Intraocular Pressure Reduction of the Latanoprost Eye Drop Compositions of Examples 1 and 2

The effects of the latanoprost eye drop compositions of Examples 1 and 2 on intraocular pressure were assessed in New Zealand white rabbits in which an increase in intraocular pressure was induced, as compared with a preservative (0.02%)-containing Xalatan®. Experiments were performed using 5 rabbits per group. The induction of the intraocular pressure elevation was performed by dropping 0.1% dexamethasone into both eyes four times a day for 4 weeks. After that, the eye drop compositions of Examples 1 and 2 and the preservative (0.02%)-containing Xalatan® were put 3 drops once a day in both eyes, respectively, so that the eyes and conjunctiva could be sufficiently wetted.

Intraocular pressure (IOP) was measured using an intraocular pressure gauge (TonoVet®, KRUUSE) before the administration (initial intraocular pressure value), and on day 0, day 3, day 7, day 10 and day 14 after the administration. At this time, the intraocular pressure of both eyes was measured 4 hours after putting eye drops.

The results are shown in Table 10 below.

TABLE 10

| Average IOP (mmHg) | Before administration (baseline) | day 0 | day 3 | day 7 | day 10 | day 14 (administration ended) |
|---|---|---|---|---|---|---|
| Example 1 | 28.3 | 25.0 | 25.1 | 23.7 | 22.2 | 22.2 |
| Example 2 | 28.2 | 25.9 | 26.6 | 25.3 | 23.8 | 23.4 |
| Preservative (0.02%) - containing Xalatan ® | 28.1 | 24.7 | 23.5 | 22.7 | 23.0 | 21.3 |

From the results of Table 10, it can be seen that the latanoprost eye drop compositions of Examples 1 and 2 exhibit the effect of the intraocular pressure reduction at a level equal to the preservative (0.02%)-containing Xalatan® which is the commercially available product.

Experimental Example 7: Effect of the Intraocular Pressure Reduction of the Latanoprost Eye Drop Composition of Example 5

The effect of the latanoprost eye drop composition of Example 5 on the intraocular pressure was evaluated in the same manner as in Experimental Example 6 in New Zealand white rabbits in which an increase in intraocular pressure was induced, compared with the preservative (0.02%)-containing Xalatan®. The results are shown in Table 11 below.

TABLE 11

| Average IOP (mmHg) | Before administration (baseline) | day 0 | day 3 | day 7 | day 10 | day 14 (administration ended) |
|---|---|---|---|---|---|---|
| Example 5 | 28.0 | 26.8 | 25.6 | 25.9 | 25.0 | 24.3 |
| Preservative (0.02%)-containing Xalatan® | 27.9 | 26.6 | 23.4 | 22.1 | 21.1 | 20.4 |

From the results of Table 11, it can be seen that the latanoprost eye drop composition of Example 5 exhibits the effect of the intraocular pressure reduction at a level equal to the preservative (0.02%)-containing Xalatan® which is the commercially available product.

Experimental Example 8: Stability of Tafluprost Eye Drop Composition According to the Content of Solubilizing Agent The eye drop compositions of Examples 10 to 12 stored in an LDPE container were stored for 2 months under semi-permeable container accelerated storage conditions (40° C., relative humidity 25%), and changes in the contents of tafluprost were confirmed. The content of tafluprost was analyzed using high performance liquid chromatography (HPLC). The results are shown in Table 12 below.

TABLE 12

| Component | Ex. 10 | Ex. 11 | Ex. 12 |
|---|---|---|---|
| Loss of tafluprost content due to container adsorption (wt %) | 5 | 16 | 8 |

From the results of Table 12 above, it can be seen that when tyloxapol was used at 0.3% or more, the loss of the content was small.

Experimental Example 9: Stability of Tafluprost Eye Drop Composition According to the Presence or Absence of Thickening Agent and Solubilizing Agent The eye drop compositions of Example 10 and Comparative Examples 6 to 7 stored in an LDPE container were stored for 2 months under semi-permeable container accelerated storage conditions (40° C., relative humidity 25%), and changes in the contents of tafluprost were confirmed. The content of tafluprost was analyzed using high performance liquid chromatography (HPLC). The results are shown in Table 13 below.

TABLE 13

| Component | Ex. 10 | Comp. Ex. 6 | Comp. Ex. 7 |
|---|---|---|---|
| Loss of tafluprost content due to container adsorption (wt %) | 5 | 25 | 7 |
| Generation amount of related substance (tafluprost acid) (wt %) | 0.1 | 3 | 1 |

From the results of Table 13 above, it can be seen that in Comparative Example 6 in which no tyloxapol was used as a solubilizing agent at the time of using sodium carboxymethylcellulose as a thickening agent, a loss of the tafluprost content of 20% or more occurred, whereas in Comparative Example 7, a loss of the tafluprost content occurred similarly as compared with Example 10, but the generation of the related substance was equivalent to or larger than 10 times. Therefore, it can be seen that the loss of the content and the generation amount of the related substance were minimum, when sodium carboxymethylcellulose and tyloxapol were used together.

Experimental Example 10: Comparison of the Stability of the Tafluprost Eye Drop Composition of the Present Invention with Commercial Product The eye drop composition of Example 10 and commercially available product, a preservative-free Taflotan®-S (Santen Pharmaceutical, stored under cold condition) stored in an LDPE container were stored for 2 months under semi-permeable container accelerated storage conditions (40° C., relative humidity 25%), and changes in the content of tafluprost and the generation of a related substance were confirmed. The content of tafluprost was analyzed using high performance liquid chromatography (HPLC). The results are shown in Table 14 below.

TABLE 14

| | Preservative-free Taflotan®-S | Ex. 10 |
|---|---|---|
| Loss of tafluprost content due to container adsorption (wt %) | 16 | 5 |
| Generation amount of related substance (tafluprost acid) (wt %) | 0.2 | 0.1 |

From the results of Table 14 above, it can be seen that in the case of the preservative-free Taflotan®-S, the main component, tafluprost, was adsorbed on the container resin, which led to the great reduction of the content of tafluprost in the eye drop composition, but the eye drop composition of Example 10 showed that the loss of the tafluprost content occurred within 5% and was relatively stable under accelerated storage conditions.

Experimental Example 11: Effect of the Intraocular Pressure Reduction of the Tafluprost Eye Drop Composition of Example 10

The effect of the tafluprost eye drop composition of Example 10 on the intraocular pressure was evaluated in the same manner as in Experimental Example 6 in New Zealand White rabbits in which an increase in intraocular pressure was induced, as compared with the preservative-free Taflotan®-S. The results are shown in Table 15 below.

TABLE 15

| Average IOP (mmHg) | Before administration (baseline) | day 0 | day 3 | day 7 | day 10 | day 14 (administration ended) |
|---|---|---|---|---|---|---|
| Example 10 | 20.1 | 25.7 | 26 | 25.3 | 24.1 | 22.8 |
| Preservative-free Taflotan® -S | 28.1 | 24.8 | 24 | 22.8 | 22.2 | 22.4 |

From the results of Table 15, it can be seen that the tafluprost eye drop composition of Example 10 exhibits the effect of the intraocular pressure reduction at a level equal to the preservative-free Taflotan®-S which is the commercially available product.

Experimental Example 12: Stability of Bimatoprost Eye Drop Composition

The eye drop composition of Example 13 stored in an LDPE container was stored for 2 months under semi-permeable container accelerated storage conditions (40° C., relative humidity 25%), and changes in the content of bimatoprost and the generation of related substances were confirmed. The content of bimatoprost and the related substance were analyzed using high performance liquid chromatography (HPLC). The results are shown in Table 16 below.

TABLE 16

| | Ex. 13 |
|---|---|
| Loss of bimatoprost content due to container adsorption (wt %) | No change |
| Total related substance (%) | No generation |

From the results of Table 16, it can be seen that the eye drop composition of Example 13 can maintain stability for a long period of time under accelerated storage conditions even though it does not contain a preservative.

Although particular embodiments of the present invention have been shown and described in detail, it will be obvious to those skilled in the art that these specific descriptions are merely preferred embodiments and the scope of the inventions is not limited thereto. It will be understood by those skilled in the art that various applications and modifications may be made based on the above description without departing from the spirit and scope of the invention.

The substantial scope of the present invention, therefore, is to be defined by the appended claims and equivalent thereof.

The invention claimed is:

1. An eye drop composition for treating glaucoma, comprising a prostaglandin analogue, a thickening agent and a solubilizing agent,
said eye drop composition comprising no preservative,
wherein the thickening agent is carboxymethylcellulose or a salt thereof, and the solubilizing agent is tyloxapol, and
wherein the eye drop composition has a viscosity at 20° C. of 3 to 15 cPs.

2. The eye drop composition for treating glaucoma according to claim 1, wherein the prostaglandin analogue is at least one selected from the group consisting of latanoprost, tafluprost, unoprostone, travoprost, and bimatoprost.

3. The eye drop composition for treating glaucoma according to claim 1, wherein the carboxymethylcellulose or a salt thereof has a viscosity of a 2% aqueous solution at 20° C. of 25 to 800 cPs.

4. The eye drop composition for treating glaucoma according to claim 1, wherein a content of carboxymethylcellulose or a salt thereof is 0.1 to 1% (w/v) based on the entire eye drop composition for treating glaucoma.

5. The eye drop composition for treating glaucoma according to claim 1, wherein a content of tyloxapol is 0.01 to 1% (w/v) based on the entire eye drop composition for treating glaucoma.

6. The eye drop composition for treating glaucoma according to claim 1, which is in a single dose form.

* * * * *